United States Patent
Finley et al.

(10) Patent No.: US 6,595,964 B2
(45) Date of Patent: Jul. 22, 2003

(54) LUER ACTIVATED THREAD COUPLER

(75) Inventors: Michael J. Finley, Wilmot, WI (US); Mark Williamson, Wonder Lake, IL (US)

(73) Assignee: Baxter International Inc., Deerfield, IL (US)

( * ) Notice: Subject to any disclaimer, the term of this patent is extended or adjusted under 35 U.S.C. 154(b) by 233 days.

(21) Appl. No.: 09/748,580

(22) Filed: Dec. 22, 2000

(65) Prior Publication Data

US 2002/0082586 A1 Jun. 27, 2002

(51) Int. Cl.[7] .......................... A61M 5/178; A61M 5/00
(52) U.S. Cl. ................ 604/246; 604/167.11; 604/905; 251/149.1
(58) Field of Search .......................... 604/246, 167.01, 604/167.02, 167.03, 167.04, 905; 251/149.1

(56) References Cited

U.S. PATENT DOCUMENTS

| | | | |
|---|---|---|---|
| 4,187,848 A | 2/1980 | Taylor | 128/247 |
| 4,607,868 A | 8/1986 | Harvey et al. | 285/332 |
| 4,617,012 A * | 10/1986 | Vaillancourt | 285/12 |
| 4,629,455 A | 12/1986 | Kanno | 604/241 |
| 4,751,619 A * | 6/1988 | Philippe et al. | 362/306 |
| 4,981,469 A | 1/1991 | Whitehouse et al. | 604/86 |
| 5,035,686 A | 7/1991 | Crittenden et al. | 604/96 |
| 5,066,286 A | 11/1991 | Ryan | 604/240 |
| 5,125,915 A | 6/1992 | Berry et al. | 604/283 |
| 5,221,272 A | 6/1993 | Proni | 604/283 |
| 5,405,340 A | 4/1995 | Fageol et al. | 604/283 |
| 5,409,125 A | 4/1995 | Kimber et al. | 215/32 |
| 5,456,284 A | 10/1995 | Ryan et al. | |
| 5,501,426 A * | 3/1996 | Atkinson et al. | 251/149.1 |
| 5,514,098 A | 5/1996 | Pfoslgraf et al. | |
| 5,536,258 A | 7/1996 | Folden | 604/265 |
| 5,549,583 A | 8/1996 | Sanford et al. | 604/283 |
| 5,620,427 A | 4/1997 | Werschmidt et al. | 604/283 |
| 5,637,101 A | 6/1997 | Shillington | 604/242 |
| 5,653,694 A | 8/1997 | Powles et al. | 604/240 |
| 5,662,231 A | 9/1997 | Adams et al. | 215/254 |
| 5,688,254 A | 11/1997 | Lopez et al. | 604/283 |
| 5,702,374 A | 12/1997 | Johnson | 604/283 |
| 5,722,545 A | 3/1998 | Rinne | 215/44 |
| 5,727,770 A | 3/1998 | Dennis | |
| 5,782,505 A | 7/1998 | Brooks et al. | 285/175 |
| 5,785,195 A | 7/1998 | Zwemer et al. | 215/329 |
| 5,806,831 A * | 9/1998 | Paradis | 251/149.1 |
| 5,817,082 A | 10/1998 | Niedospial, Jr. et al. | 604/414 |
| 5,855,568 A | 1/1999 | Battiato et al. | 604/240 |
| 5,924,865 A * | 7/1999 | Quinn | 433/127 |

* cited by examiner

Primary Examiner—Henry Bennet
Assistant Examiner—Alfred Basichas
(74) Attorney, Agent, or Firm—Jeffrey C. Nichols; Mark J. Buonaiuto; Francis C. Kowalik

(57) ABSTRACT

A coupler for receiving a threaded male luer fitting in sealed relationship includes a housing having an attachment end, a conduit end opposite the attachment end and defining a central passageway for providing fluid communication between the luer fitting and a conduit. An arrangement is attached to the housing for establishing a sealed connection between a luer tip and the central passageway. The conduit end has a relatively larger diameter than the attachment end and defines a shoulder at a junction of the attachment end and the conduit end. A resilient member is disposed on the attachment end adjacent the shoulder for exerting an axially directed compressive force upon the male luer fitting as it is threadably engaged upon the attachment end.

22 Claims, 2 Drawing Sheets

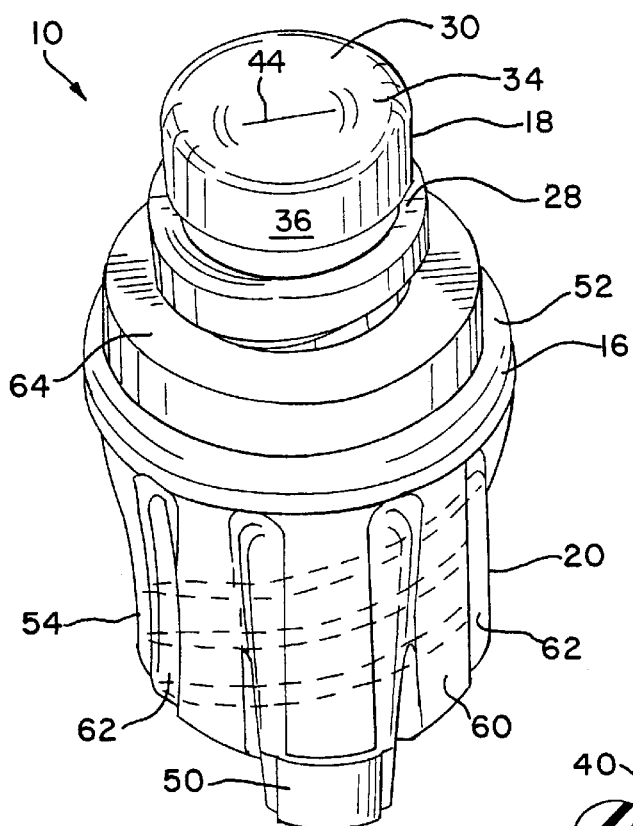
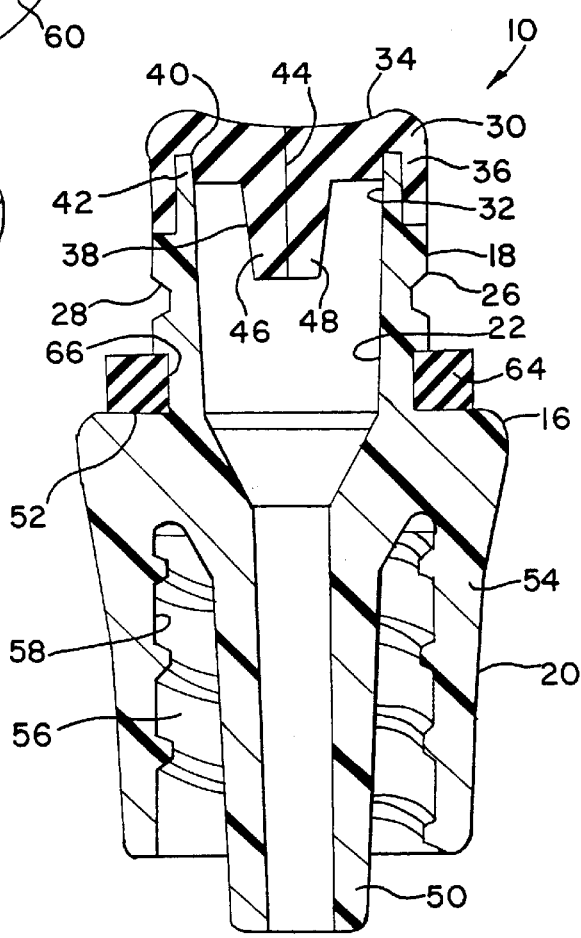
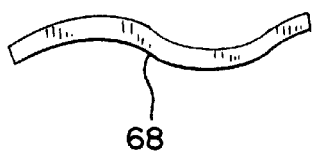

LUER ACTIVATED THREAD COUPLER

FIELD OF THE INVENTION

The present invention relates generally to needleless fluid connection devices, and more specifically to a device for repeatedly establishing a sealed connection to a conduit or a container for medical applications.

BACKGROUND OF THE INVENTION

One very prevalent form of health care therapy is infusion or intravenous ("I.V.") therapy, whereby fluids possessing desired medication or other characteristics are infused into a patient over varying lengths of time. To practice this infusion therapy, frequently a connection needs to be made for the transfer of fluid between two components, along a fluid passageway and eventually to a patient. As an example, administration sets are widely used to administer liquids parenterally to a patient and other medical devices are connected to the administration set to provide the proper administration.

One widely used connector for making such connections is a luer connection assembly. In the luer connection assembly, a male luer tip component or fitting having a frustoconical shape is inserted into a female luer component or fitting having a frustoconical shaped receiving cavity. Opposing conical surfaces come into contact with each other to form a sealed friction fit.

Until the connection is made, the passageway through each of the luer fittings and into the lumen of a component attached to the luer fitting is open to the environment. This lumen, and the passageway through the luer connectors, form a portion of the fluid passageway and must be sterile prior to use. During use, the lumen and passageway must be sealed against microbial ingress during use. Thus, these connection assemblies and the associated components are packaged in sterile packaging and the connections are typically made just prior to establishing fluid communication with a patient's venous system.

There are two general types of luer connection assemblies. One type is generally referred to as the luer slip, where the connection is maintained by the friction fit between the male luer tip and female luer component. The other type is generally referred to as a luer lock connection, whereby the male luer tip is encircled by an annular locking flange having a threaded internal surface. The female component includes a corresponding thread formed about the outer surface. Engaging the threaded flange to the threaded outside surface establishes the connection between the male luer tip and female component while preventing accidental disconnects.

To insure a universal luer connection among components provided by various manufacturers, universal standards have been developed, designated by American National Standards Institute, Inc. (ANSI) and International Organization for Standardization (ISO). These standards include prescribed dimensions for male slip and luer lock assemblies. These standards include the thread pitch (threads per inch) of the respective couplings.

Other standards in the ISO regulations include performance requirements for luer connections. One such requirement is that after a luer lock type connection is made, to prevent inadvertent disconnection, the luer connection should resist an axial removal force of 8 pounds and an unscrewing torque of at least 3 in-oz without disconnection. The luer connection should also hold a seal against 45 psi after a connection torque of 16 in-oz has been applied. In luer slip connections, the unscrewing torque is supplied by the friction between the mated, opposing conical surfaces.

Once a component of I.V. therapy is placed in fluid communication with the body, the fluid passageway should be sealed from the environment to prevent contamination, and this passageway should also be sealed so as to not allow any leakage of bodily fluids into the environment. However, most therapies require periodic access to the fluid passageway. Because the portion of the fluid passageway through a female luer connection component is open to the environment, these components will not form a sealed connection to the fluid passageway unless the fluid passageway is placed in fluid communication with the body by means of a male luer connector.

In one prevalent example of intravenous therapy, fluid containing a drug in solution is injected into a primary flow of fluid from an I.V. solution container through an administration set to a catheter extending within a vein. The drug containing fluid may be injected from a syringe, secondary medication set or the like, into the set where it mixes with the flowing fluid. In another example, fluid is injected directly into or withdrawn from a catheter extending within the body. In addition, the catheters are flushed periodically to maintain patency by the injection of small amounts of saline or heparin.

As can be appreciated, it is highly desirable to maintain catheters and administration sets in service as long as possible without compromising the safety of the patient. Replacement of catheters and sets is time consuming and expensive. Therefore, over the period of time of use of a set or catheter there may be many connections and disconnects. For example, there may be over 100 connections and disconnects to a connection site on a catheter or set before the catheter or set is replaced. In addition, a connection may be made and that connection maintained for an extended period of time before disconnection. For example, a connection may be made for up to seven days of "indwell" and yet the connection should still be capable of accepting intermediate and subsequent connections and disconnects without allowing leakage to the environment.

To facilitate repeated connections which are sufficiently secure to meet prescribed industry and medical standards, the thread design of the luer fittings must be easy to manipulate by medical personnel, while still providing a strong and sturdy connection.

A known design criteria of luer lock fittings is that it is common for there to be at least as much as a 0.0188 inch difference in thread tolerances between the threads of various manufacturers. Thus, some luer thread engagements will be relatively looser or "sloppier" than others. Thus, the engagement of the threads may not supply the desired unscrewing torque. On the other hand, if the thread engagement is too tight, excessive stress may be exerted on the locking flange extending about the male luer fitting, and the flange may be cracked or otherwise damaged.

Thus, there is a need for a threaded or luer lock coupling which better accommodates a range of thread dimensions to preserve the sealing characteristics of the connection.

Accordingly, a main object of the present invention is to provide an improved threaded luer lock coupling which is configured to maintain thread interference between adjacent threads of a male and female luer fittings.

Another object of the present invention is to provide an improved threaded luer lock coupling featuring the ability to exert an acceptable axial compressive force on the male luer fitting to enhance thread friction and the resulting sealing relationship.

Yet another object of the present invention is to provide an improved threaded luer lock coupling incorporating a resilient member which accommodates adequate tightening torque by the male luer fitting upon the female fitting.

BRIEF SUMMARY OF THE INVENTION

The above-listed objects are met or exceeded by the present luer activated thread coupler, which is designed to enhance the sealing relationship between a male luer fitting and a peripheral catheter or similar medical conduit. To create a thread interference between the respective threads of the male luer fitting and the female or receiving coupler fitting, the present invention features a resilient washer disposed on an externally threaded attachment end of the coupler. When a male luer fitting is threadably engaged on the attachment end, the luer tip engages a penetrable seal on the receiving coupler, establishing fluid communication between the luer fitting and a conduit or catheter. The resilient washer creates an axially directed compressive force against the male luer threads which forces them against the threads of the attachment end, thus enhancing the sealing relationship between the two components. At the same time, excessive radial forces are not exerted upon the locking collar of the male luer fitting.

More specifically, the present invention provides a coupler for receiving a threaded male luer fitting in sealed relationship, and includes a housing having an attachment end, a conduit end opposite the attachment end and defines a central passageway for providing fluid communication between the luer fitting and a conduit. An arrangement is attached to the housing for establishing a sealed connection between a luer tip and the central passageway. The conduit end has a relatively larger diameter than the attachment end and defines a shoulder at a junction of the attachment end and the conduit end. A resilient member is disposed on the attachment end adjacent the shoulder for exerting an axially directed compressive force upon the male luer fitting as it is threadably engaged upon the attachment end.

In the preferred embodiment, the resilient member is a washer which circumscribes the attachment end, however a leaf spring is also contemplated, and the resealable penetrable member is a slitted septum valve with a "duck-bill" type seal.

BRIEF DESCRIPTION OF THE SEVERAL VIEWS OF THE DRAWINGS

FIG. 1 is a top perspective view of the present thread coupler;

FIG. 2 is a vertical section taken along the line 2—2 of FIG. 1 and in the direction indicated;

FIG. 2A is a side elevational view of a wave washer suitable for use with the present coupler;

DETAILED DESCRIPTION OF THE INVENTION

Figure 3:
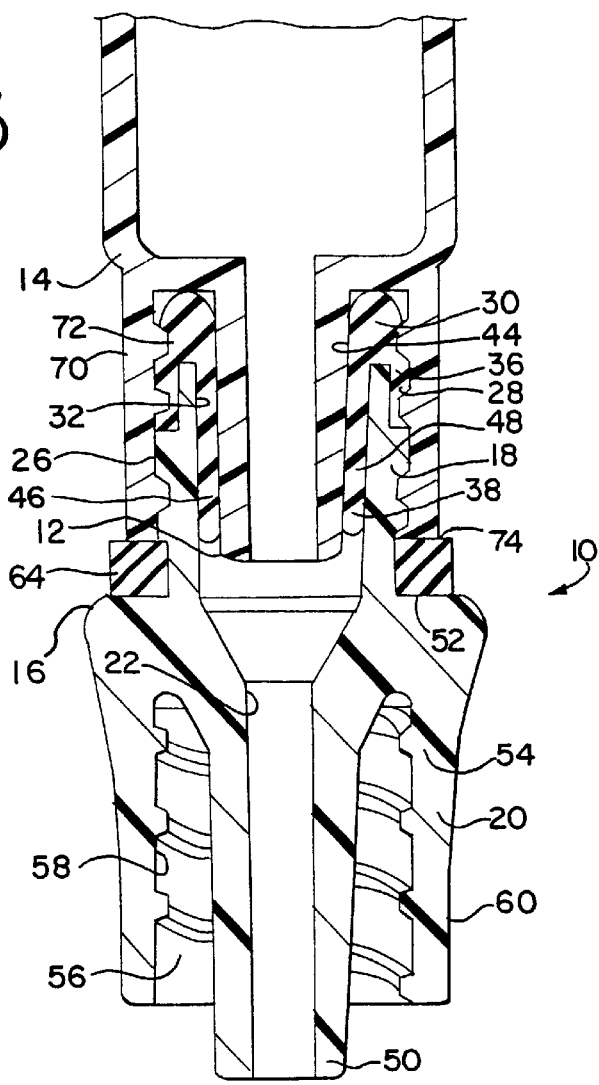
FIG. 3 is a vertical sectional view of the present coupler threadably engaged with a male luer fitting.

Referring now to FIGS. 1 and 2, the coupler of the present invention is generally designated 10, and is a female luer or receiving coupler, which engages a penetrating male luer pin 12 of a male luer fitting 14 (FIG. 3). The coupler 10 includes a housing 16 having an attachment end 18 for attachment to the male luer fitting 14 and a conduit end 20 opposite the attachment end for connection to a peripheral catheter, medical tubing or other conduit in fluid communication with a flow of fluid to or from a body. A central passageway 22 is defined by the housing 16, for providing fluid communication between the luer fitting 14 and a conduit 24. In the preferred embodiment, the housing 16 is the end of a syringe, and is made of a rigid plastic material such as DN003 from Eastar of Kingsport, Tenn., however other suitable rigid, medically suitable plastics are contemplated, as are other configurations of delivery components.

The attachment end 18 has an outer surface 26 provided with helical threads 28 configured to receive the male luer fitting 14, and to be consistent with ISO standards. Thus, overall, the attachment end 18 has the appearance of a threaded nipple.

An arrangement is attached to the housing 16 for establishing a sealed connection between a luer tip and the central passageway 22. In the preferred embodiment, this arrangement is a resilient resealable penetrable valve member 30, which is sealingly secured in an opening 32 in the attachment end 18, and is configured to receive the male luer pin 12. The member 30 may also be characterized as a resealable preslit septum valve, having a generally disk-shaped upper portion 34, an annular skirt 36 for attachment to the housing 16, and a lower portion 38 extending axially downward within said passageway. The skirt 36 is configured to have a tight friction fit about the opening 32 and is further secured thereon by ultrasonic or radio frequency welding, chemical adhesives, or other known and medically appropriate fastening technologies. In the preferred embodiment, the member 30 has an annular recess 40 for being located on an upper edge 42 of the housing 16.

A slit 44 extends through both the upper portion 34 and the lower portion 38, and divides the lower portion into a pair of flaps 46, 48. In the closed position, shown in FIG. 2, the member 30 is made of a resilient material such that the flaps 46, 48 are forced together to seal the slit 44 closed. However, the slit 44 and flaps 46, 48 are configured to sealingly accommodate the insertion of a male luer pin 12 (FIG. 3). More specifically, it is preferred that the resealable penetrable member 30 is formed of an elastic, resilient chlorinated polyisoprene material provided by Lexington Medical of Rock Hill, S.C., however, other flexible medically suitable elastomeric materials are contemplated. It is anticipated that lubricating the member 30 should facilitate insertion of the luer tip 18. Such lubrication may be applied while forming the slit or by other means such as incorporating the lubrication into the septum material or by applying lubricious coatings to the top surface. One known lubricant is silicon oil produced by Dow Corning of Midland, Mich.

It will be seen that the central passageway 22 has a larger diameter at the attachment end 18 to accommodate the insertion of the male luer pin 12. At the conduit end 20, the diameter of the passageway 22 narrows to a tubular portion 50 which is dimensioned to permit insertion into the conduit 24.

The exterior dimensions of the coupler 10 are the opposite from the passageway 22, for the attachment end 18 has a relatively smaller diameter than the conduit end 20. A generally planar shoulder 52 is defined at a junction of the attachment end 18 and the conduit end 20.

Depending from the shoulder 52 is an annular skirt 54 which defines an annular space 56 between an inside surface 58 of the skirt and the tubular portion 50 of the passageway 22. In the preferred embodiment, the inside surface 58 of the skirt 54 is threaded to facilitate connection to certain types of conduits 24. It is also preferred that an outside surface 60 of the skirt 54 is provided with positive gripping formations such as flutes 62.

An important feature of the present coupler 10 is the provision of a resilient member 64 disposed on the attachment end 18, preferably adjacent the shoulder 52. The function of the member 64 is to exert an axially directed compressive force upon the male luer fitting 14 as it is threadably engaged upon the attachment end 18 without exerting an excessive force on the male luer fitting. In the preferred embodiment, the resilient member 64 is a washer configured to circumscribe the attachment end 18 and made of resilient polymeric material. The specific material, and its hardness or Durometer value, will depend on the application, as will the diameter and thickness of the washer. In a most preferred embodiment, the resilient member 64 is made of medical grade silicon having a Durometer value of approximately 60. A corresponding recess 66, configured to receive and retain the washer 64, is formed in the base of the attachment end 18 adjacent the shoulder 52. It will be seen that the shoulder 52 also preferably forms a seat for the washer 64. An acknowledged equivalent alternative to the resilient washer 64 is a wave washer 68 (FIG. 2A).

Referring now to FIG. 3. the present coupler 10 is shown operationally engaged to the male luer fitting 14. It will be seen that the luer pin 12 has sealingly displaced the flaps 46, 48 to create a fluid communication pathway between the luer fitting 14 and the passageway 22. In achieving this connection, a locking flange 70 having threads 72 engages the corresponding threads 28 on the attachment end 18. An advantage of the present washer 64 is that an axially directed force is directed against the respective threads 72, 28 while note directing excessive radial forces against the locking flange 70.

Figure 4:
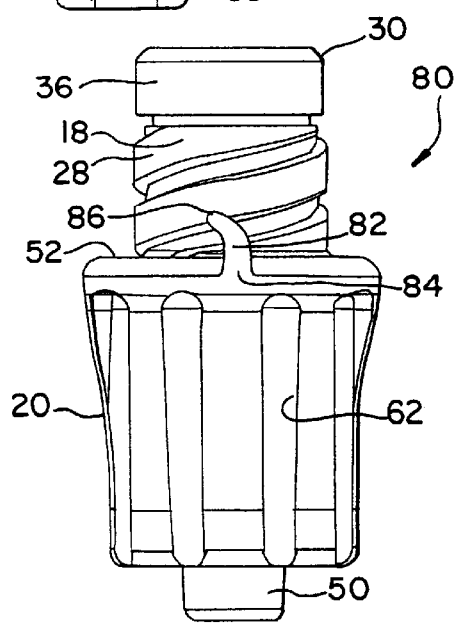
FIG. 4 is a side elevational view of an alternate embodiment of the coupler of FIG. 1.

Referring now to FIG. 4, an alternate embodiment of the present coupler is generally designated 80. Shared components with the coupler 10 are designated with identical reference numbers. The main difference between the coupler 80 and the coupler 10 is that the coupler 80 lacks the resilient washer 64 and instead, features a leaf spring 82 which generally extends coaxially with the attachment end 18. In the preferred embodiment, the spring 82 is integrally molded onto the shoulder 52, and a pair of such springs 82 are provided. In shape, the spring 82 has a relatively wide base 84 and a narrow tip 86. The tip 86 is configured to engage the end 74 of the locking flange 72 in the same manner as the washer 64.

In operation, as the locking flange 70 progresses axially toward the shoulder 52, an end 74 of the flange comes into contact with the resilient member 64. The resilience of the member 64 will exert sufficient, axially-directed compressive force on the male luer fitting 14 to create a back pressure and resulting thread interference on the engaged threads 72, 28 of the male fitting and the attachment end, respectively. This engagement forces the opposing threads 72, 28 into a tight, frictional engagement. Another advantage of this arrangement is that variations in manufacturers' thread tolerances are accommodated for by the resilient member 64, which is dimensioned to be thick enough to exert sufficient force to compensate for such variations. Still another advantage of the resilient member 64 is that it impedes unwanted removal by more securely maintaining the threaded engagement of the fitting 14 upon the attachment end 18 without creating radial forces directly against the locking flange 70.

While a particular embodiment of the luer activated thread coupler of the invention has been shown and described, it will be appreciated by those skilled in the art that changes and modifications may be made thereto without departing from the invention in its broader aspects and as set forth in the following claims.

What is claimed is:

1. A coupler for receiving a threaded male luer fitting in sealed relationship, comprising:

a housing having an attachment end, a conduit end opposite said attachment end and defining a central passageway for providing fluid communication between the luer fitting and a conduit, said attachment end being provided with threads, having a base forming a recess and configured as an externally threaded nipple;

an arrangement attached to said housing for establishing a sealed connection between a luer tip and said central passageway;

said conduit end being of relatively larger diameter than said attachment end and defining a shoulder at a junction of said attachment end and said conduit end; and a resilient member disposed on said attachment end adjacent said shoulder being retained upon said housing by at least one of said threads and engagement with said recess, said resilient member exerting an axially directed compressive force upon the male luer fitting as it is threadably engaged upon said attachment end.

2. The coupler as defined in claim 1 wherein said resilient member is a washer which circumscribes said attachment end.

3. The coupler as defined in claim 1 wherein said resilient member is a leaf spring.

4. The coupler as defined in claim 1 wherein said resilient member exerts sufficient compressive force on the male luer fitting to create a back pressure and resulting thread interference on engaged threads of the male fitting and said attachment end.

5. The coupler as defined in claim 1 wherein said conduit end is configured for releasable connection of said passageway to a conduit in fluid communication with the human body.

6. The coupler as defined in claim 5 wherein said passageway is tubular and said conduit end has an annular skirt extending from said shoulder and defining an annular space between an inside surface of said skirt and a tubular portion of said passageway.

7. The coupler as defined in claim 6 wherein said inside surface of said skirt is threaded.

8. The coupler as defined in claim 6 wherein said skirt has an exterior surface having textured positive gripping formations.

9. The coupler as defined in claim 1 wherein said arrangement is a resealable preslit septum valve.

10. The coupler as defined in claim 9 wherein said septum valve has a generally disk-shaped upper portion and a lower portion extending axially downward within said passageway, and a slit extending through both said upper portion and said lower portion.

11. The coupler as defined in claim 10 wherein said slit is configured for sealingly receiving the male luer fitting.

12. A coupler for receiving a threaded male luer fitting in sealed relationship, comprising:

a housing having an attachment end being provided with threads, a base forming a recess, and a conduit end opposite said attachment end and defining a central passageway for providing fluid communication between the luer fitting and a conduit;

said attachment end configured as an externally threaded nipple and having a resilient resealable penetrable valve member sealingly secured therein;

said conduit end being of relatively larger diameter than said attachment end and defining a shoulder at a junction of said attachment end and said conduit end;

a resilient member disposed on said attachment end adjacent said shoulder being retained upon said housing by at least one of said threads and engagement with said recess, said member being attached to an outer surface of said housing having said threads, said resilient member creating thread interference between said threads of said attachment end and the male luer fitting.

13. The coupler as defined in claim 12 wherein said resilient member is a washer which circumscribes said attachment end.

14. The coupler as defined in claim 12 wherein said resilient member is a leaf spring.

15. The coupler as defined in claim 1 wherein said resilient member is fixed to said attachment end and to said shoulder.

16. The coupler as defined in claim 1 wherein said resilient member is retained in position on said attachment end between said threads and said shoulder and is thus prevented from axial movement relative to said housing.

17. The coupler as defined in claim 15 wherein said resilient member has a Durometer value selected to be sufficiently resilient for preventing movement of threads of the male luer fitting and said attachment end.

18. The coupler as defined in claim 1 wherein said diameters are configured so that said shoulder is externally located on said housing.

19. The coupler as defined in claim 17 wherein said Durometer value is approximately 60 Durometers.

20. The coupler as defined in claim 12 wherein said resilient member is fixed to said attachment end and to said shoulder.

21. The coupler as defined in claim 20 wherein said resilient member has a Durometer value selected to be sufficiently resilient for preventing relative movement of threads of the male luer fitting and said threads of said attachment end.

22. The coupler as defined in claim 12 wherein said resilient member is retained in position on said attachment end between said threads and said shoulder and is thus prevented from axial movement relative to said housing.

* * * * *